(12) United States Patent
Runglertkriangkrai

(10) Patent No.: US 9,126,057 B2
(45) Date of Patent: Sep. 8, 2015

(54) HAIR CONDITIONING COMPOSITION COMPRISING CATIONIC SURFACTANT SYSTEM AND DIRECT DYE

(75) Inventor: Siriporn Runglertkriangkrai, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 364 days.

(21) Appl. No.: 12/635,826

(22) Filed: Dec. 11, 2009

(65) Prior Publication Data

US 2010/0150858 A1 Jun. 17, 2010

Related U.S. Application Data

(60) Provisional application No. 61/121,918, filed on Dec. 12, 2008.

(51) Int. Cl.
| | | |
|---|---|---|
| *A61Q 5/12* | (2006.01) | |
| *A61K 8/18* | (2006.01) | |
| *A61K 8/34* | (2006.01) | |
| *A61K 8/41* | (2006.01) | |
| *A61K 8/46* | (2006.01) | |
| *A61Q 5/06* | (2006.01) | |

(52) U.S. Cl.
CPC . *A61Q 5/12* (2013.01); *A61K 8/342* (2013.01); *A61K 8/416* (2013.01); *A61K 8/463* (2013.01); *A61Q 5/065* (2013.01)

(58) Field of Classification Search
CPC ....... A61K 8/463; A61K 8/342; A61K 8/416; A61Q 5/12; A61Q 5/065
See application file for complete search history.

(56) References Cited

U.S. PATENT DOCUMENTS

| | | | |
|---|---|---|---|
| 4,678,475 A | 7/1987 | Hoshowski et al. | |
| 4,964,874 A | 10/1990 | Saphakkul | |
| 5,110,318 A | 5/1992 | Altobelli | |
| 6,274,126 B1 | 8/2001 | Newell et al. | |
| 7,988,955 B2 | 8/2011 | Molenda et al. | |
| 2001/0014317 A1 | 8/2001 | Pyles | |
| 2002/0015685 A1 | 2/2002 | Pascual | |
| 2002/0143063 A1 | 10/2002 | Alvarado | |
| 2003/0039623 A1 | 2/2003 | Pyles | |
| 2004/0158939 A1 | 8/2004 | Wells | |
| 2005/0015895 A1 | 1/2005 | Azizova | |
| 2006/0096041 A1* | 5/2006 | Molenda et al. | 8/405 |
| 2007/0010408 A1* | 1/2007 | Uehara | 510/119 |

FOREIGN PATENT DOCUMENTS

| | | |
|---|---|---|
| DE | 19641841 | 10/1997 |
| DE | 29722988 | 5/1999 |
| DE | 29903100 | 9/2000 |
| EP | 1502578 B1 | 4/2009 |
| GB | 2385056 A | 8/2003 |
| JP | 04334313 | 11/1992 |
| JP | 05043438 | 2/1993 |
| JP | 05194161 | 8/1993 |
| JP | 06271434 | 9/1994 |
| JP | 2000128750 | 5/2000 |
| JP | 2004059565 | 2/2004 |
| JP | 2006104162 | 4/2006 |
| WO | WO2006044208 | 4/2006 |

OTHER PUBLICATIONS

International Search Report; PCT/US2009/065491; Mailing Date Dec. 1, 2011; 15 pages.

* cited by examiner

*Primary Examiner* — Abigail Fisher
*Assistant Examiner* — Daniel L Branson
(74) *Attorney, Agent, or Firm* — Linda M. Sivik

(57) ABSTRACT

Disclosed is a hair conditioning composition comprising: a cationic surfactant system of either (i) or (ii): (i) the system comprising: a salt of a mono-long alkyl quaternized ammonium and an anion wherein the anion is selected from the group consisting of C1-C4 alkyl sulfate, and mixtures thereof; and a di-long alkyl quaternized ammonium salt; or (ii) the system comprising: salts of mono-long alkyl amines wherein the mono-long alkyl group has 20 to about 24 carbon atoms; and a di-long alkyl quaternized ammonium salt; a high melting point fatty compound; a direct dye; and an aqueous carrier. The composition of the present invention provides improved coloring benefits, while providing conditioning benefits.

10 Claims, No Drawings

HAIR CONDITIONING COMPOSITION COMPRISING CATIONIC SURFACTANT SYSTEM AND DIRECT DYE

CROSS REFERENCE TO RELATED APPLICATIONS

This application claims the benefit of U.S. Provisional Application No. 61/121,918 filed on Dec. 12, 2008.

FIELD OF THE INVENTION

The present invention relates to a hair conditioning composition comprising: a cationic surfactant system of either (i) or (ii): (i) the system comprising: a salt of a mono-long alkyl quaternized ammonium and an anion wherein the anion is selected from the group consisting of C1-C4 alkyl sulfate, and mixtures thereof; and a di-long alkyl quaternized ammonium salt; or (ii) the system comprising: salts of mono-long alkyl amines wherein the mono-long alkyl group has 20 to about 24 carbon atoms; and a di-long alkyl quaternized ammonium salt; a high melting point fatty compound; a direct dye; and an aqueous carrier. The composition of the present invention provides improved coloring benefits, while providing conditioning benefits.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. For example, some cationic surfactants, when used together with some high melting point fatty compounds, are believed to provide a gel matrix which is suitable for providing a variety of conditioning benefits such as slippery feel during the application to wet hair and softness and moisturized feel on dry hair.

There is a need for hair conditioning compositions which provide coloring benefits while providing conditioning benefits. Such coloring benefit is, for example, at least one of the followings: coloring to non-colored hair, color enhancing of colored hair, preventing color fade of colored hair and grey blending.

A variety of attempts has been made for providing both hair coloring and hair conditioning benefits. For example, Japanese Patent Application Laid-open No. H5-43438 discloses a coloring hair treatment composition comprising 0.3% of Behentrimonium Chloride, 0.1% of Cetyltrimonium Chloride, 0.1% of Distearyldimonium Chloride, 10% of Behenyl alcohol, and 0.05% of an acidic dye.

However, it has been found that it is still not easy to obtain hair conditioning compositions which provide coloring benefits, while providing conditioning benefits.

Based on the foregoing, there remains a need for hair conditioning compositions which provide improved coloring benefits while providing conditioning benefits.

None of the existing art provides all of the advantages and benefits of the present invention.

SUMMARY OF THE INVENTION

The present invention is directed to a hair conditioning composition comprising by weight:
(a) from about 0.2% to about 10% of a cationic surfactant system of either (i) or (ii):
(i) the system comprising: a salt of a mono-long alkyl quaternized ammonium and an anion wherein the anion is selected from the group consisting of C1-C4 alkyl sulfate, and mixtures thereof; and a di-long alkyl quaternized ammonium salt; or
(ii) the system comprising: salts of mono-long alkyl amines wherein the mono-long alkyl group has 20 to about 24 carbon atoms; and a di-long alkyl quaternized ammonium salt.
(b) from about 1% to about 15% of a high melting point fatty compound;
(c) from about 0.00005% to about 0.5% of a direct dye; and
(d) an aqueous carrier.

The conditioning compositions of the present invention provide improved coloring benefits, while providing conditioning benefits.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Composition

It is believed that; by the use of the specific cationic surfactant system, the composition of the present invention can provide improved coloring benefits, while providing conditioning benefits, compared to other cationic surfactant systems such as those using behenyltrimethylammonium chloride with a di-alkyl quaternary ammonium salt.

Preferably, the composition of the present invention is substantially free of anionic surfactants and anionic polymers, in view of compatibility with cationic surfactants, and stability of the gel matrix when formed by cationic surfactants and high melting point fatty compounds. In the present invention, "substantially free of anionic surfactants and anionic polymers" means that the composition contains 1% or less, preferably 0.5% or less, more preferably totally 0% of total of anionic surfactants and anionic polymers.

Cationic Surfactant System

The composition of the present invention comprises a cationic surfactant system. The cationic surfactant is included in the composition at a level by weight of from about 0.2% to about 10%, preferably from about 0.3% to about 8%, more preferably from about 0.4% to about 5%, in view of providing conditioning benefits and improved coloring benefits together with high melting point fatty compounds and direct dyes.

The cationic surfactant system is either:
(i) the system comprising: a salt of a mono-long alkyl quaternized ammonium and an anion wherein the anion is selected from the group consisting of C1-C4 alkyl sulfate, and mixtures thereof; and a di-long alkyl quaternized ammonium salt; or
(ii) the system comprising: salts of mono-long alkyl amines wherein the mono-long alkyl group has 20 to about 24 carbon atoms; and a di-long alkyl quaternized ammonium salt. The system (i) is preferably used in view of providing the benefit of the present invention especially conditioning and color benefits at the same time. The compounds, which can be used in the cationic surfactant system of the present invention, are explained below in detail.

In the system, it is preferred that the weight ratio of the di-long alkyl cationic surfactant to the mono-long alkyl cationic surfactant is within the range of from about 1:1 to about 1:20, more preferably from about 1:1 to about 1:15, still more preferably from about 1:1 to about 1:10, in view of providing conditioning benefits and improved coloring benefits.

Mono-Long Alkyl Quaternized Ammonium Alkyl Sulfate Salt

Mono-long alkyl quaternized ammonium alkyl sulfate salts use herein are those having the formula (I):

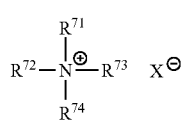
(I)

wherein one of $R^{71}$, $R^{72}$, $R^{73}$ and $R^{74}$ is selected from an aliphatic group of from 16 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of C1-C4 alkyl sulfate, preferably methyl sulfate ($CH_3OSO_3$) which can be called as methosulfate, ethyl sulfate ($C_2H_5OSO_3$) which can be called as ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 16 to 30 carbon atoms, more preferably from 18 to 26 carbon atoms, still more preferably from 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Among them, more preferred cationic surfactants are those having a longer alkyl group, i.e., C18-22 alkyl group. Such cationic surfactants include, for example, behenyl trimethyl ammonium methyl sulfate or ethyl sulfate and stearyl trimethyl ammonium methyl sulfate or ethyl sulfate, and still more preferred is behenyl trimethyl ammonium methyl sulfate or ethyl sulfate. It is believed that; cationic surfactants having a longer alkyl group provide improved smoothness and soft feeling on wet and dry hair, compared to cationic surfactant having a shorter alkyl group. It is also believed that such cationic surfactants can provide reduced irritation, compared to cationic surfactants having a shorter alkyl group.

Mono-Long Alkyl (C20-24) Amine Salts

Mono-long alkyl (C20-24) amine salts useful herein are those of: (i) primary, secondary, and tertiary amines wherein the amines have one long alkyl or alkenyl group of from about 20 to about 24 carbon atoms; and (ii) acids selected from the group consisting of 1-glutamic acid, lactic acid, hydrochloric acid, malic acid, succinic acid, acetic acid, fumaric acid, tartaric acid, and mixtures thereof. The amines and acids are included in the compositions at a level such that the mole ratio of the amines to the acids is preferably from about 1:0.3 to about 1:2, more preferably from about 1:0.3 to about 1:1.3, still more preferably from about 1:0.4 to about 1:1.

The primary, secondary, and tertiary amines useful herein are, for example, those having the following formula:

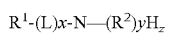

wherein $R^1$ is a straight or branched alkyl or alkenyl group of from about 20 to about 24 carbon atoms, preferably a straight alkyl group; L is a linkage selected from amido, amidoalkyl, amidopolyoxyalkyl, polyoxyalkyl, and mixtures thereof, wherein the alkyl has from 1 to 4 carbon atoms, preferably selected from amido or amidoalkyl in which the alkyl has from 1 to 4 carbon atoms; x is an integer of 0 or 1, preferably 1; $R^2$ is a C1 to C4 alkyl, alkenyl, alkoxyl, hydroxyalkyl, or polyoxyalkylene; y is an integer of from 0 to 2, preferably 2; z is an integer of form 0 to 2, preferably 0; y+z is an integer of 2.

Highly preferred amine is a tertiary amidoamine having the following general formula:

$R^1CONH(CH_2)mN(R^2)_2$ wherein $R^1$ is a straight or branched alkyl or alkenyl group of from about 20 to about 24 carbon atoms, preferably a straight alkyl group; m is an integer from 1 to 4; and $R^2$ is a C1 to C4 alkyl, alkenyl, alkoxyl, hydroxyalkyl, or polyoxyalkylene, preferably alkyl.

Such tertiary amidoamine useful herein include, for example: behenamidopropyldimethylamine, behenamidopropyldiethylamine, behenamidoethyldiethylamine, behenamidoethyldimethylamine, behenamidobutyldimethylamine, behenamidobutyldiethylamine, arachidamidopropyldimethylamine, arachidamidopropyldiethylamine, arachidamidoethyldiethylamine, arachidamidoethyldimethylamine, arachidamidobutyldimethylamine, and arachidabutyldiethylamine.

Di-Long Alkyl Quaternized Ammonium Salt

Di-long alkyl quaternized ammonium salts useful herein are those having the formula (I):

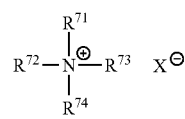
(I)

wherein two of $R^{71}$, $R^{72}$, $R^{73}$ and $R^{74}$ is selected from an aliphatic group of from 16 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and X⁻ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 16 to 40 carbon atoms, more preferably from 16 to 26 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof. Preferably, the anion is selected from the group consisting of halides such as chloride and mixtures thereof.

Such di-long alkyl quaternized ammonium salts useful herein include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound is included in the composition at a level of from about 1% to about 15%, preferably from about 3% to about 10%, more preferably from about 5% to about 8% by weight of the composition, in view of providing conditioning benefits such as slippery feel during the application to wet hair, softness and moisturized feel on dry hair.

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Direct Dye

The composition of the present invention comprises a direct dye. The direct dye is included in the composition at a level of from about 0.00005% to about 15.0%, preferably from about 0.0001% to about 10.0%, more preferably from about 0.001% to about 5.0% by weight of the composition, in view of providing color benefit without changing original hair color tone, and minimizing the staining during application.

The direct dyes are those which are also called as non-oxidative dyes. The direct dyes useful herein include, for example: nonionic dyes such as nitro dyes, azo dyes, and anthraquinone dyes; cationic dyes such as basic dyes; and anionic dyes such as acidic dyes. It is known that some azo dyes and anthraquinone dyes can be classified as cationic dyes or anionic dyes, when they have cationic or anionic substitutions. The dye can be used alone or in combination with other dyes, according to target color of hair to which the composition is applied.

Preferably, the direct dyes useful herein are nonionic direct dyes, cationic direct dyes, and mixtures thereof, in view of compatibility with cationic surfactants. Anionic dyes, when used, are preferably combined with nonionic direct dyes and/or cationic direct dyes.

In some shades, it is preferred to use mixtures of nonionic direct dyes and cationic direct dyes, more preferably mixtures of nitro dyes and basic dyes. In such shades, it is believed that; the combination of nonionic dyes and cationic dyes, especially the combination of nonionic nitro dyes and cationic basic dyes can provide evenness on hair color, minimized stain on hands, and prolonged color benefits.

Nonionic nitro dyes useful herein include, for example, 1,4-bis-[(2-hydroxyethyl)amino]-2-nitrobenzene, 1-(2-hydroxyethyl)amino-2-nitro-4-[di-(2-hydroxyethyl)amino] benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC) 5 Blue No. 12), 1-[(2,3-dihydroxypropyl)amino]-4-[methyl-(2-hydroxyethyl) amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di-(2-hydroxyethyl)amino]-2-nitrobenzene (HC Violet No. 2), 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di-(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di-(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino] benzoic acid, 2-chloro-6-ethylamino-4-nitrophenol, 2-amino-6-chloro-4-nitrophenol, 4-[(3-hydroxypropyl) amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1, 4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), and 2,4-dinitro-1-hydroxynaphthalene.

Other nonionic direct dyes useful herein include, for example, 1,4-di-[(2,3-dihydroxypropyl)amino]-9,10-anthraquinone, 1,4-di-[(2-hydroxyethyl)amino]-9,10-anthraquinone (CI61545, Disperse Blue 23), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-9,10-anthraquinone (HC Red No. 8), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), N-(6-((3-chloro-4-(methylamino)phenyl)imino)-4-methyl-3-oxo-1,4-cyclohexadien-1-yl)urea (HC Red No. 9), 2-((4-(di-(2-hydroxyethyl)amino)phenyl)amino)-5-((2-hydroxyethyl) amino)-2,5-cyclohexadien-1,4-dione (HC Green No. 1), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis-(dicyanomethylidene)indane, 1-[di-(2-hydroxyethyl)amino]-3-methyl-4-[(4-nitrophenyl)azo]benzene (CI1210, Disperse Red No. 17), 1-[di-(2-hydroxyethyl)amino]-4-[(4-nitrophenyl)azo]benzene, (Disperse Black No. 9), 4-[(4-aminophenyl)azo]-1-[di-(2-hydroxyethyl)amino]-3-methylbenzene (HC Yellow No. 7), 2,6-diamino-3-[(pyridin-3-yl)azo]-pyridine and 2-((4-(ethyl-(2-hydroxyethyl)amino)-2-methylphenyl)azo)-5-nitro-1,3-thiazole (CI111935; Disperse Blue No. 106).

Cationic basic dye useful herein includes, for example, di-[4-(diethylamino)phenyl][4-(ethylamino)naphthyl]carbenium chloride (CI42595; Basic Blue No. 7), di-[4-(dimethylamino)phenyl][4-(phenylamino)naphthyl]carbenium chloride (CI44045; Basic Blue No. 26), Basic Blue No. 77, 8-amino-2-bromo-5-hydroxy-4-imino-6-[(3-(trimethylammonio)-phenyl)amino]-1(4H)-naphthalenone chloride (CI56059; Basic Blue No. 99), tri-(4-amino-3-methylphenyl) carbenium chloride (CI42520; Basic Violet No. 2), di-(4-aminophenyl)(4-amino-3-methylphenyl)carbenium chloride (CI42510; Basic Violet No. 14), 1-[(4-aminophenyl)azo]-7-(trimethylammonio)-2-naphthol chloride (CI12250; Basic Brown No. 16), 3-[(4-amino-2,5-dimethoxyphenyl)azo]-N,N,N-trimethylbenzenaminium chloride (CI12605, Basic Orange No. 69), 1-[(4-amino-2-nitrophenyl)azo]-7-(trimethylammonio)-2-naphthol chloride (Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl) azo]-7-(trimethylammonio)naphthalene chloride (CI12245; Basic Red No. 76), 3-methyl-1-phenyl-4-[(3-(trimethylammonio)phenyl)azo]pyrazol-5-one chloride (CI12719; Basic Yellow No. 57), and 1-methyl-4-((methylphenyl-hydrazono) methyl)pyridinium methyl sulfate (Basic Yellow No. 87).

Other cationic direct dyes useful herein include, for example, Benzenamine, 4-[(2,6-Dichlorophenyl)(4-Imino-3,5-Dimethyl-2,5-Cyclohexadien-1-ylidene)Methyl]-2,6-Dimethyl-, Phosphate) (HC Blue No. 15), 1-(2-morpholiniumpropylamino)-4-hydroxy-9,10-anthraquinone methyl sulfate, and 1-[(3-(dimethylpropylaminium)propyl)amino]-4-(methylamino)-9,10-anthraquinone chloride.

Anionic direct dyes useful herein include, for example, disodium bis[4-(N-ethyl-N-3-sulfonatophenylmethyl)aminophenyl]phenylmethylium (INCI name: Acid Blue 9), Benzenesulfonic acid, 2-[(9,10-Dihydro-4-hydroxy-9,10-Dioxo-1-anthracenyl)amino]-5-methyl-monosodium salt (INCI name: Ext. Violet 2). p-((2-Hydroxy-1-naphthyl)azo)benzenesulfonic acid sodium salt (INCI name: Orange 4), 2,2'-(1, 4-Anthraquinonylenediimino)bis(5-methylbenzenesulfonic acid) disodium salt (INCI name: ACID GREEN 25), Acides 2-(2-quinoleyl) 1,3-indanedione mono, di, trisulfoniques, sodium salt (INCI name: Yellow 10), 5-amino-4-hydroxy-30 (phenylazo)-2,7-naphthalenesulfonic acid, disodium salt (INCI name: Acid Red 33).

Aqueous Carrier

The conditioning composition of the present invention comprises an aqueous carrier. The level and species of the carrier are selected according to the compatibility with other components, and other desired characteristic of the product. Generally, the compositions of the present invention comprise from about 20% to about 99%, preferably from about 30% to about 95%, and more preferably from about 80% to about 95% water.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product.

Gel Matrix

Preferably, the above cationic surfactants, together with high melting point fatty compounds and an aqueous carrier, form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6, more preferably form about 1:1 to about 1:4.

Silicone Compound

Preferably, the compositions of the present invention contain a silicone compound. It is believed that the silicone compound can provide smoothness and softness on dry hair.

The silicone compounds herein can be used at levels by weight of the composition of preferably from about 0.1% to about 20%, more preferably from about 0.15% to about 10%, still more preferably from about 0.2% to about 8%.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferably, the silicone compounds have an average particle size of from about 1 microns to about 50 microns, in the composition.

Preferably, silicone compounds useful herein include amino substituted materials. Preferred aminosilicones include, for example, those which conform to the general formula (III):

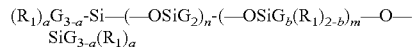

$(R_1)_a G_{3-a}\text{-Si}—(—OSiG_2)_n\text{-}(—OSiG_b(R_1)_{2-b})_m—O—SiG_{3-a}(R_1)_a$ wherein G is hydrogen, phenyl, hydroxy, or C1-C8 alkyl, preferably methyl; a is an integer having a value from 1 to 3, preferably 1; b is 0, 1 or 2, preferably 1; n is a number from 1 to 2,000, preferably from 100 to 2,000, more preferably from 300 to 1,800; m is an integer from 0 to 1,999, preferably from 0 to 10, more preferably 0; $R_1$ is a monovalent radical conforming to the general formula $C_q H_{2q} L$, wherein q is an integer having a value from 2 to 8 and L is selected from the following groups: $—N(R_2)CH_2—CH_2—N(R_2)_2$; $—N(R_2)_2$; $—N(R_2)_3 A^-$; $—N(R_2)CH_2—CH_2—NR_2H_2 A^-$; wherein $R_2$ is hydrogen, phenyl, benzyl, or a saturated hydrocarbon radical, preferably an alkyl radical from about $C_1$ to about $C_{20}$; $A^-$ is a halide ion.

One highly preferred amino silicones are those corresponding to formula (III) wherein m=0, a=1, q=3, G=methyl, n is preferably from about 1500 to about 1700, more preferably 1600; and L is $—N(CH_3)_2$ or $—NH_2$, more preferably $NH_2$. Another highly preferred amino silicones are those corresponding to formula (III) wherein m=0, a=1, q=3, G=methyl, n is preferably from about 400 to about 600, more preferably about 500; and L is $—N(CH_3)_2$ or $—NH_2$, more preferably $—NH_2$. Such highly preferred amino silicones can be called as terminal aminosilicones, as one or both ends of the silicone chain are terminated by nitrogen containing group. It is believed that, such terminal aminosilicone can provide balanced benefit between conditioning benefits and clean feel, compared to other silicones such as graft aminosilicones and silicones having no amino substitution.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C.

Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

The other silicone compounds useful herein include polyalkyl or polyaryl siloxanes with the following structure:

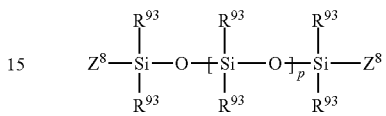

$$Z^8—\underset{R^{93}}{\overset{R^{93}}{Si}}—O—\left[\underset{R^{93}}{\overset{R^{93}}{Si}}—O\right]_p—\underset{R^{93}}{\overset{R^{93}}{Si}}—Z^8$$

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The other silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

The silicone compounds may further be incorporated in the present composition in the form of an emulsion, wherein the emulsion is made by mechanical mixing, or in the stage of synthesis through emulsion polymerization, with or without the aid of a surfactant selected from anionic surfactants, nonionic surfactants, cationic surfactants, and mixtures thereof.

Among the variety of the silicone compounds, a combination of graft aminosilicones and silicone resins may also be preferred to provide durable conditioning and chronic/long lasting color protection benefit. Such durable conditioning and chronic/long lasting color protection benefits are, for example, at least one of the followings: maintaining good sensory feel long period after coloring hair, preventing color fading of colored hair or minimizing/slowing down color lost until next coloring hair. Such combination of graft aminosilicones and silicone resins may be preferably used in combination with the above aminosilicone of the formula (III). Such graft aminosilicones and silicone resins are described below in detail.

(i) Graft Aminosilicone

The graft aminosilicone can be included in the composition at levels by weight of the composition of from about 0.25% to about 15%, more preferably from about 0.5% to about 10%, still more preferably from about 1% to about 7%.

The aminosilicone useful herein include, but are not limited to silicones of the following structure:

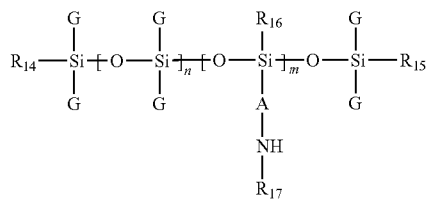

wherein:

a sum (n+m) ranges from about 2 to about 2000, preferably from about 150 to about 2000, more preferably from about 250 to about 1200, still more preferably from about 300 to about 800; n is a number ranging from about 1 to about 1999, and m is a number ranging from about 1 to about 1999; and n and m are chosen such that a ratio of m:n is from about 1:1000 to about 1:10, preferably from about 1:1000 to about 1:25, more preferably from about 1:800 to about 1:50, still more preferably from about 1:500 to about 1:50, even more preferably from about 1:400 to about 1:100;

$R_{14}$, $R_{15}$, $R_{16}$, which may be identical or different, are chosen from a hydroxyl radical, C1-C4 alkoxy radicals and methyl, preferably $R_{14}$ and $R_{15}$ are hydroxyl radical and/or C1-C4 alkoxy radicals and $R_{16}$ is methyl;

A is chosen from linear and branched C3-C8 alkenyl radicals;

$R_{17}$ is chosen from H, phenyl, linear or branched C1-C4 alkyl radical, benzyl or preferably linear or branched (C2-C8)$NH_2$; and G is chosen from H, phenyl, hydroxyl, C1-C8 alkyl, preferably methyl.

These aminosilicones may be of the random or block type.

Suitable aminosilicones of the present invention include, but are not limited to, organomodified silicones with amine functionality available commercially under the trade names such as ADM1100 and ADM1600 from Wacker Silicones, AP6087, DC2-8211, DC8822, DC8822A, DC8803, DC2-8040, DC2-8813, DC2-8630 and DC8566 from Dow Corning Corporation, KF-862, KF-861, KF-862S, KF-8005, KF-8004, KF-867S, KF-873, and X-52-2328 from Shin-Etsu Corporation, and TSF 4702, TSF 4703, TSF 4704, TSF 4705, TSF 4707. TSF 4708, TSF 4709, F42-B3115, SF 1708, SF 1923, SF 1921, SF 1925, OF TP AC3309, OF 7747, OF-NH TP AI3631, OF-NH TP AI3683 from GE Bayer Silicones.

Highly preferred aminosilicones of the present invention are organomodified silicones with amine functionality with viscosities of greater than about 4,000 mPa·s in view of conditioning efficiency and up to about 100,000 mPa·s in view of friendly incorporation processing and spreadability, which include, but are not limited to, commercially available fluids under the trade names ADM1100 from Wacker Silicones, AP6087, DC8803 from Dow Corning Corporation, and TSF 4707 from GE Bayer Silicones.

(ii) Silicone Resin

Without wishing to be bound by theory, silicone resins are believed to create a 3-dimensional network within the aminosilicone fluid giving rise to viscoelasticity thereby improving the adhesive properties of the fluid and hence the durability on a fibrous substrate. Preferably, the silicone resin is insoluble in water. In the case that the fiber treatment composition is an emulsion, the mixture of the aminosilicone and the silicone resin may be dispersed therewithin in the form of emulsified droplets.

Preferably, the organosiloxane resins according to the invention are solid at about 25° C. Whilst not wishing to be bound to theory, it is believed that solid silicone resin can form an ultrafine dispersion in the aminosilicone which behaves unlike any of the silicone resin per se, the aminosilicone per se, and a blended fluid with the aminosilicone when using fluid silicone resin.

Preferably, the organosiloxane resins according to the invention have a molecular weight range of from about 500 to about 50,000, more preferably from about 750 to about 25,000, still more preferably from about 1,000 to about 10,000 grams/mole. Whilst not wishing to be bound to theory, it is believed that silicone resins of lower or larger molecular weight tend to provide reduced synergy with the aminosilicone.

The silicone resin can be included in the composition at levels by weight of the composition of from about 0.0001% to about 10%, preferably from about 0.001% to about 5%, more preferably from about 0.002% to about 3%, still more preferably from about 0.003% to about 1%. It is preferred to contain the silicone resin such that the weight ratio of the silicone resin to the aminosilicone is within the scope of from about 1:500 to about 1:3000, more preferably from about 1:800 to about 1:2000, still more preferably from about 1:800 to about 1:1500. It is believed that a lower level of the silicone resin provides reduced synergetic benefit with the aminosilicone, while a higher level of the silicone resin tend to provide poor sensory feel.

Organosiloxane resins useful herein are combinations of $R_3SiO_{1/2}$, "M" units, $R_2SiO$ "D" units, $RsiO_{3/2}$, "T" units, $SiO_2$ "Q" units in ratios to each other that satisfy the relationship $R_nSiO_{(4-n)/2}$ where n is a value between 1.0 and 1.50 and R is a methyl group. Silanol or alkoxy functionalities may also be present in the resin structure.

More preferably, the organosiloxane resins comprise repeating monofunctional $R_3SiO_{1/2}$, "M" units and the quadrafunctional $SiO_2$ "Q" units, otherwise known as "MQ" resins. In this case, the ratio of the "M" to "Q" functional units is advantageously from 0.7 and the value of n is 1.2. Organosiloxane resins such as these are commercially available as SR1000 available from GE Bayer Silicones and Wacker 803 from Wacker Silicones.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: cationic conditioning polymers including, for example, cationic celluloses such as polyquaternium-10, and cationic guar gums; low melting point oils having a melting point of less than 25° C. including, for example, unsaturated fatty alcohols such as oleyl alcohol and ester oils such as pentaerythritol ester oils; polyethylene glycols; other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and Phenoxyethanol; pH adjusting agents, such as citric acid, sodium citrate, succinic acid, phosphoric acid, sodium hydroxide, sodium carbonate; salts, in general, such as potassium acetate and sodium chloride; perfumes; sequestering agents, such as ethylenediamine tetra acetic acid and its salts; and ultraviolet and infrared screening and absorbing agents such as octyl salicylate, octyl methoxycinnamate, benzophenone-3 and benzophenone-4.

Product Forms

The conditioning compositions of the present invention can be in the form of rinse-off products or leave-on products, and can be formulated in a wide variety of product forms, including but not limited to creams, gels, emulsions, mousses and sprays.

The conditioning composition of the present invention is especially suitable for rinse-off hair conditioner. Such compositions are preferably used by following steps:

(i) after shampooing hair, applying to the hair an effective amount of the conditioning compositions for conditioning the hair; and (ii) then rinsing the hair.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

[Compositions]

| Components | Ex. 1 | Ex. 2 | Ex. 3 | Ex. 4 | Ex. 5 | Ex. 6 | Ex. i | Ex. ii |
|---|---|---|---|---|---|---|---|---|
| Behenyl trimethyl ammonium methyl sulfate | 1.1 | 1.5 | 2.0 | — | — | 1.1 | — | — |
| Behenamidopropyldimethylamine | — | — | — | 2.3 | 2.5 | — | — | 2.3 |
| 1-glutamic acid | — | — | — | 0.6 | 0.7 | — | — | 0.6 |
| Behenyl trimethyl ammonium chloride | — | — | — | — | — | — | 1.1 | — |
| Dicetyl dimethyl ammonium chloride | 0.35 | — | 0.60 | 0.35 | 0.50 | 0.35 | 0.35 | — |
| Distearyl dimethyl ammonium chloride | — | 0.35 | — | — | — | — | — | — |
| Polyquaternium-10 *1 | — | — | — | — | 0.2 | — | — | — |
| Cetyl alcohol | 0.9 | 1.2 | 1.5 | 2.5 | 3.0 | 0.9 | 0.9 | 2.5 |
| Stearyl alcohol | 2.3 | 3.3 | 4.0 | 4.5 | 5.0 | 2.3 | 2.3 | 4.5 |
| Aminosilicone-1 *2 | — | 0.5 | — | — | — | 0.5 | — | — |
| Dimethicone blend *3 | — | — | 4.2 | — | — | — | — | — |
| Dimethicone/Cyclomethicone *4 | — | — | — | — | 4.2 | — | — | — |
| Aminosilicone-2 *5 | — | — | — | — | — | 3.5 | — | — |
| MQ resin *6 | — | — | — | — | — | 0.0035 | — | — |
| Basic Brown 16 | — | 0.008 | — | — | 0.008 | 0.008 | — | — |
| HC Blue No. 15 | — | 0.0004 | — | — | 0.0004 | 0.0004 | — | — |
| HC Red No 10 | 0.07 | 0.006 | 0.04 | 0.07 | 0.006 | 0.006 | 0.07 | 0.07 |
| 4-Amino-3-Nitrophenol | 0.07 | 0.005 | 0.06 | 0.07 | 0.005 | 0.005 | 0.07 | 0.07 |
| UV absorbers | — | — | 0.1 | — | — | — | — | — |
| Preservatives | 0.4 | 0.4 | 0.4 | 0.4 | 0.4 | 0.4 | 0.4 | 0.4 |
| Perfume | 0.4 | 0.4 | 0.4 | 0.4 | 0.4 | 0.4 | 0.4 | 0.4 |
| Panthenol | — | — | 0.03 | — | 0.03 | — | — | — |

-continued

| Components | Ex. 1 | Ex. 2 | Ex. 3 | Ex. 4 | Ex. 5 | Ex. 6 | Ex. i | Ex. ii |
|---|---|---|---|---|---|---|---|---|
| Panthenyl ethyl ether | — | — | 0.03 | — | 0.03 | | — | — |
| Deionized Water | | | | q.s. to 100% | | | | |

Definitions of Components
*1 Polyquaternium-10: Polymer JR30M available from Amerchol
*2 Aminosilicone-1: Terminal aminosilicone which is available from GE having a viscosity 10,000 mPa·s, and having following formula (III): $(R_1)_aG_{3-a}$-Si—$(—OSiG_2)_n$-O—$SiG_{3-a}(R_1)_a$ (III) wherein G is methyl; a is an integer of 1; n is a number from about 400 to about 600; $R_1$ is a monovalent radical conforming to the general formula $CqH_{2q}L$, wherein q is an integer of 3 and L is —$NH_2$
*3 Dimethicone blend: a blend of dimethicone having a viscosity of 18,000,000 mPa·s and dimethicone having a viscosity of 200 mPa·s available from GE Toshiba
*4 Dimethicone/Cyclomethicone: a blend dimethicone having a viscosity of 18,000,000 mPa·s and cyclopentasiloxane available from GE Toshiba
*5 Aminosilicone-2: ADM1100 from Wacker Silicones
*6 MQ resin: SR1000 (Polytrimethyl hydrosilylsilicate) from GE Silicones Method of Preparation The conditioning compositions of "Ex. 1" through "Ex. 6", "Ex. i" and "Ex. ii" as shown above can be prepared by any conventional method well known in the art. They are suitably made as follows:

Cationic surfactants, high melting point fatty compounds and direct dyes are added to water with agitation, and heated to about 80° C. The mixture is cooled down to about 50° C. If included, silicone compounds, perfumes, preservatives are added to the mixture with agitation. Then the mixture is cooled down to room temperature.

Examples 1 through 6 are hair conditioning compositions of the present invention which are particularly useful for rinse-off use. The embodiments disclosed and represented by the previous "Ex. 1" through "Ex. 6" have many advantages. For example, they provide color benefits while providing conditioning benefits. They are especially suitable for red or brown colored hair.

Coloring Benefit

With respect to the above compositions of Ex. 1, Ex. 4, Ex. i and Ex. ii, a coloring benefit is evaluated by the following method. Results of the evaluation are also shown below in Table 1.

Color Deposition

Color deposition is evaluated as follows:

i) The color of non-treated, non-colored hair sample (hereinafter Color N) is measured using an instrument called X-Rite SP64 Spectrophotometer.

ii) The sample is treated with the composition 15 times as follows:

1 g of the composition is applied and evenly spread to the sample, then rinsed off from the sample. Then the sample is dried.

iii) After 15 cycle of the treatments, the color of the treated hair sample (hereinafter Color T) is measured using an instrument called X-Rite SP64 Spectrophotometer.

iv) The L, a, b values for Color N and Color T are then compared to calculate the $DE_{2000}$ measurements.

TABLE 1

|  | Ex. 1 | Ex. i |
|---|---|---|
| Color deposition | A1 | C1 |

A1: Above 14% (excluding 14%) to 30% increase of color deposition, compared to Control (C1)
B1: Up to 14% (including 14%) increase of color deposition, compared to Control (C1)
C1: Control

TABLE 2

|  | Ex. 1 | Ex. 4 | Ex. ii |
|---|---|---|---|
| Color deposition | A2 | A2 | C2 |

A2: Above 14% (excluding 14%) to 30% increase of color deposition, compared to Control (C2)
B2: Up to 14% (including 14%) increase of color deposition, compared to Control (C2)
C2: Control The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair dye conditioning composition comprising by weight:
    (a) from about 0.2% to about 10% of a cationic surfactant system:
        the system comprising: a salt of a mono-long alkyl quaternized ammonium and an anion wherein the anion is selected from the group consisting of C1-C4 alkyl sulfate, and mixtures thereof; and a di-long alkyl quaternized ammonium salt;
    (b) from about 1% to about 15% of a high melting point fatty compound having a melting point of 25° C. or higher;
    (c) from about 0.00005% to about 0.5% of a direct dye; and
    (d) an aqueous carrier;

wherein the weight ratio of the di-long akyl quaternized ammonium salt to the salt of a mono-long alkyl quaternized ammonium and an anion is within the range of from 1:1 to 1:10; and wherein the salt of a mono-long alkyl ammonium and an anion is selected from the group consisting of behenyl trimethyl ammonium methyl sulfate, behenyl trimethyl ammonium ethyl sulfate, and mixtures thereof, and wherein the di-long alkyl quaternized ammonium salt is selected from the group consisting of dicetyl dimethyl ammonium chloride, distearyl dimethyl ammonium chloride, and mixtures thereof.

2. The conditioning composition of claim 1 further comprising from about 0.1% to about 20% of a silicone compound.

3. The conditioning composition of claim 2, wherein the silicone compound is aminosilicone compound.

4. The conditioning composition of claim 1 further comprising: (e) from about 0.1% to about 20% of a graft aminosilicone; and (f) from about 0.0001% to about 10% of a silicone resin.

5. The conditioning composition of claim 1 wherein the composition contains 1% or less of anionic surfactants and anionic polymers.

6. The conditioning composition of claim 1 which is a rinse-off hair conditioning composition.

7. The conditioning composition of claim 1 wherein the direct dye is selected from the group consisting of nonionic dyes, azo dyes, anthraquinone dyes, cationic dyes and anionic dyes and mixtures thereof.

8. The conditioning composition of claim 1 wherein the high melting point fatty compound is a fatty alcohol and the fatty alcohol is selected from the group consisting of cetyl alcohol, stearyl alcohol, behenyl alcohol, and mixtures thereof.

9. The conditioning composition of claim 1 wherein the direct dye is the combination of nonionic nitro dyes and cationic basic dyes.

10. The conditioning composition of claim 1 wherein the composition comprises from about 80% to about 95% water.

* * * * *